(12) United States Patent
Woodham

(10) Patent No.: US 10,203,304 B2
(45) Date of Patent: Feb. 12, 2019

(54) GEL ELECTROPHORESIS AND TRANSFER COMBINATION USING CONDUCTIVE POLYMERS AND METHOD OF USE

(71) Applicant: Woodham Biotechnology Holdings, LLC, Beverly Hills, CA (US)

(72) Inventor: Andrew Woodham, Belmont, MA (US)

(73) Assignee: Woodham Biotechnology Holdings, LLC, Beverly Hills, CA (US)

( * ) Notice: Subject to any disclaimer, the term of this patent is extended or adjusted under 35 U.S.C. 154(b) by 111 days.

(21) Appl. No.: 15/639,317

(22) Filed: Jun. 30, 2017

(65) Prior Publication Data

US 2017/0363574 A1 Dec. 21, 2017

Related U.S. Application Data

(62) Division of application No. 15/186,110, filed on Jun. 17, 2016, now Pat. No. 9,702,851.

(51) Int. Cl.
*G01N 27/447* (2006.01)

(52) U.S. Cl.
CPC . *G01N 27/44739* (2013.01); *G01N 27/44713* (2013.01); *G01N 27/44726* (2013.01); *G01N 27/44747* (2013.01); *G01N 27/44778* (2013.01)

(58) Field of Classification Search
CPC ....... G01N 27/44739; G01N 27/44782; G01N 27/453
See application file for complete search history.

(56) References Cited

U.S. PATENT DOCUMENTS 4,702,371 A 10/1987 Hoshi
4,840,714 A 6/1989 Littlehales
(Continued)

FOREIGN PATENT DOCUMENTS

EP 1632772 A1 3/2006
WO WO2009131257 A1 10/2009
(Continued)

OTHER PUBLICATIONS

Murat Ates, Tolga Karazehir, A. Sezai Serac, "Conducting polymers and their applications." Current Physical Chemistry 2.3 (2012): 224-240.

*Primary Examiner* — Alexander S Noguerola
(74) *Attorney, Agent, or Firm* — Trojan Law Offices

(57) ABSTRACT

A precast gel and blotting membrane combination unit and method of use. The device includes two plates, each plate having a conductive opaque region with conductive polymers and a transparent region having static-dissipative polymers. Between the plates are a gel matrix and blotting membrane. The device is placed in a tank capable of both performing the electrophoresis phase and transfer phase of a western blot. During the electrophoresis phase, current flows from a pair of electrophoresis electrodes to separate proteins by size. The user can visualize the extent of protein separation by observing a tracking dye through the transparent region. After the electrophoresis phase, voltage is switched to a pair of transfer phase electrodes. The device allows current to flow through the conductive opaque regions of the plates to transfer separated proteins to a blotting membrane directly after electrophoresis without having to remove or reorient the device in the tank.

2 Claims, 8 Drawing Sheets

(56) References Cited

U.S. PATENT DOCUMENTS

| | | |
|---|---|---|
| 4,994,166 A | 2/1991 | Fernwood |
| 5,102,524 A | 4/1992 | Dutertre |
| 5,120,419 A | 6/1992 | Papp |
| 5,268,568 A | 12/1993 | Lee |
| 5,449,446 A | 9/1995 | Verma |
| 5,593,561 A | 1/1997 | Cognard |
| 5,609,315 A | 3/1997 | Lepore |
| 6,602,391 B2 | 8/2003 | Serikov |
| 7,645,369 B2 | 1/2010 | Hoeltke |
| 8,029,657 B1 | 10/2011 | Wu |
| 8,173,002 B2 | 5/2012 | Margalit |
| 8,702,950 B2 | 4/2014 | Maruo |
| 2003/0032201 A1 | 2/2003 | Flesher |
| 2006/0042951 A1 | 3/2006 | Ohse |
| 2007/0284250 A1 | 12/2007 | Magnant |
| 2013/0105206 A1 | 5/2013 | Kim |
| 2014/0131205 A1 | 5/2014 | Margalit |
| 2015/0083594 A1 | 3/2015 | Asare-Okai |
| 2016/0231272 A1* | 8/2016 | McKee ............ G01N 27/44739 |

FOREIGN PATENT DOCUMENTS

| | | |
|---|---|---|
| WO | WO2010135364 A2 | 11/2010 |
| WO | WO2011106693 A2 | 9/2011 |
| WO | WO2012027219 A1 | 3/2012 |
| WO | WO2015016194 A1 | 1/2014 |
| WO | WO2015058462 A1 | 4/2014 |

* cited by examiner

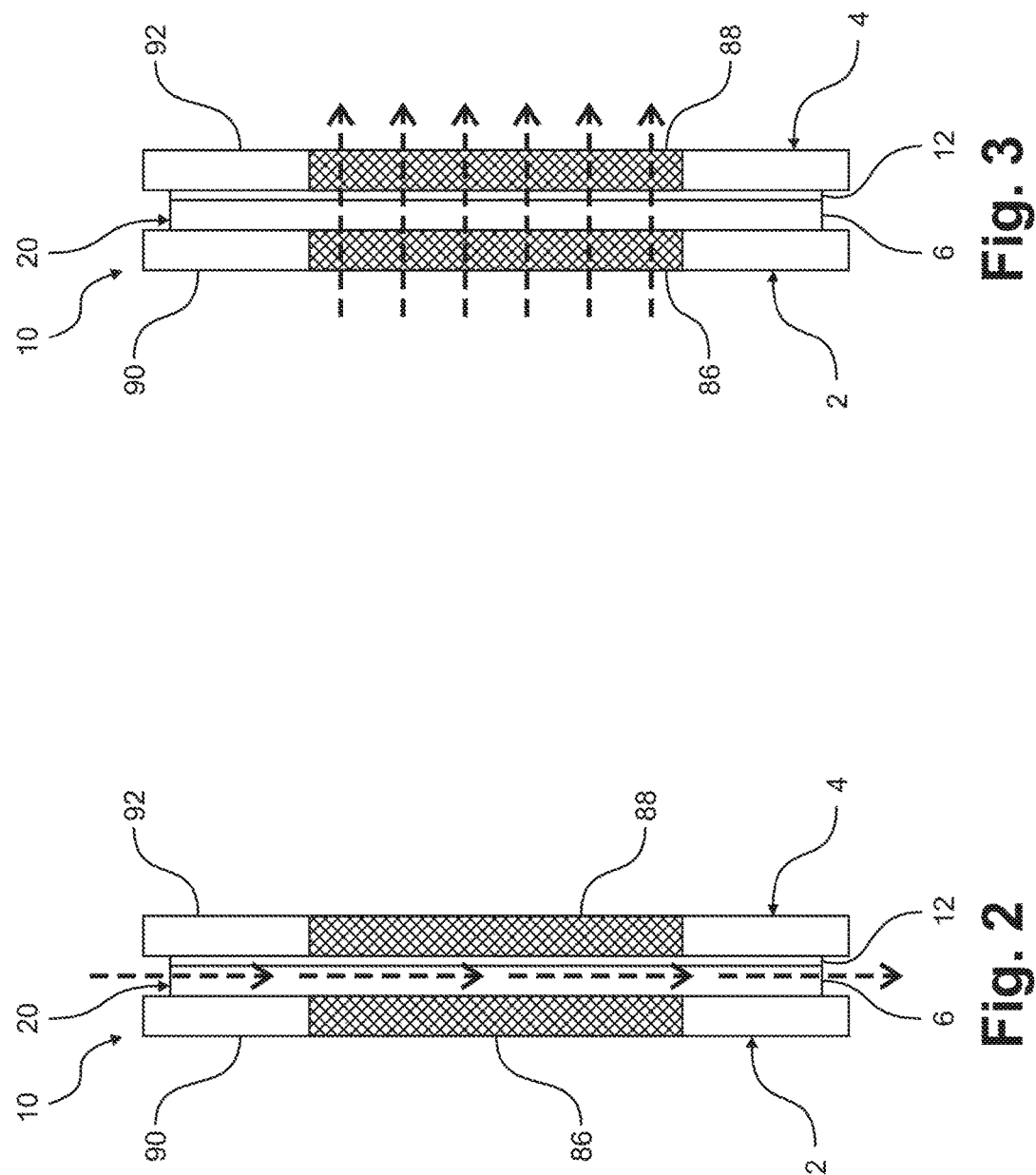

GEL ELECTROPHORESIS AND TRANSFER COMBINATION USING CONDUCTIVE POLYMERS AND METHOD OF USE

CROSS REFERENCE TO RELATED APPLICATIONS

This application is a division of, and claims priority to, U.S. patent application Ser. No. 15/186,110, entitled "Gel Electrophoresis and Transfer Combination Using Conductive Polymers and Method of Use," filed Jun. 17, 2016, the contents of which are incorporated by reference.

FIELD OF THE INVENTION

The present invention relates generally to gel electrophoresis and transfer with a precast gel and blotting membrane combination unit using conductive polymers.

BACKGROUND OF THE INVENTION

Although western blotting is a common technique, there are still many issues that arise from the protein transfer step. These difficulties include the introduction of air bubbles when placing gels on membranes, and the gels often tear when they are transferred from a precast or other casted gel setting to a separate protein transfer membrane, especially in the case of thinner gels that are employed to reduce the amount of protein needed. These complications can be devastating when the availability of the protein sample is limited, no more protein is available, or when the protein is a clinical specimen. The source of many of the problems with the prior art can be traced to the need to remove the gel from the gel cassette in order to accomplish the transfer step. It has not been possible to eliminate this step in the prior art because the gel cartridges are made of materials that are non-conductive/insulative and are used to support the gels. Additionally, researchers often prefer to watch the electrophoretic step progress, which has limited the motivation to invent electrophoretic gel systems incorporating non-transparent conductive materials.

It would be desirable to have a one-step separation and transfer western blot apparatus and method of separating and transferring proteins that utilize a single combination of a precast gel and protein transfer membrane. Hence, it would be advantageous to have a means to avoid the introduction of air bubbles, and to avoid the tearing of gels during transfer.

There have been many attempts to simplify the separation and transfer of proteins for analysis using various types of apparati and techniques. U.S. Pat. No. 4,994,166 to Fernwood et al. describes a single apparatus for slab gel electrophoresis and blotting, both of which are performed in a single tank cell, which contains separation electrodes along opposing vertical walls, and blotting electrodes arranged horizontally above and below the level of gel placement. The cell is operated in separatory and blotting modes, in which separatory and blotting electrodes are separately energized. Fernwood requires porous gel supports to allow the electric field to pass through the membrane. In addition, the top plate transfer electrode must be removed from contact with the buffer solution during the protein separatory phase.

U.S. Pat. No. 5,102,524 to Dutertre describes a multiple electrophoresis method, where different sets of electrodes are used in a two-step process to first separate biomolecules and then to transfer them to a deposition membrane.

U.S. Pat. No. 5,593,561 to Cognard describes a multiple electrophoresis method for controlled migration of biomolecules and transfer thereof to a membrane in a vessel, containing a plurality of parallel elongated electrodes. The first electric field, established between electrodes, provides means for macromolecular separation in a gel, and the second electric field, perpendicular to the first, provides means for transferring the biomolecules onto the membranes. In the described method, electrodes and transfer membranes are first assembled in the vessel, which is then filled with gel. After the separation of biomolecules in the gel, and the proteins are transferred to the membrane, the gel is liquefied, dissolved, or decomposed, which allows for the removal of the membrane. Cognard's invention is for use without prefabricated gel and membrane combination units.

U.S. Pat. No. 8,173,002 to Margalit describes a dry blotting system to transfer proteins onto a transfer membrane. The system does not include an electrophoresis device, so the device does not allow the user to visualize the separation and transfer phases in a single device. The device requires the user to transfer the gel to a transfer membrane on the blotting device. Margalit teaches the use of electrically conducting polymers, but not in combination with a single device that both separates proteins and transfers the proteins to a transfer membrane.

U.S. Patent Appl. Pub. No. 2006/0042951 to Ohse discloses an apparatus to separate and transfer proteins via the use of a fine groove, a transferring electrode, and a transparent conductive material having a thickness of approximately 0.1 µm. The apparatus includes a pair of separating electrodes for causing a substance in a sample to move along a passage, and a pair of transferring electrodes for causing the substance in the sample to be transferred to the capturing material by electrophoresis. The conductive material is not capable of serving as the support structure due to its thickness of approximately 0.1 µm, which would not have sufficient strength to serve effectively as the supporting walls for a gel. The separation and blotting is performed in an electrophoresis buffer and does not make use of a gel slab or gel slab assembly, which are commonly used for western blots.

U.S. Pat. No. 6,602,391 to Serikov discloses an apparatus and method for capillary separation of biomolecules and post-separation blotting. However, Serikov does not disclose the use of a slab gel where the user can view the separation of biomolecules and transfer the macromolecule to a blotting membrane for western blotting.

Conductive polymers have previously been described, but not in conjunction with electrophoresis and blotting. Ates et al. Describes various applications of conducting polymers in "Conducting Polymers and their Applications" (Current Physical Chemistry, 2012, 2, 224-240). International Pat. Appl. No. PCT/EP2013/065163 to Jung discloses a conductive polymer composition and transparent electrode for an antistatic layer. International Pat. Appl. No. PCT/KR2008/002236 to Kim discloses a conductive polymer for use as a transparent electrode and a method of fabricating the electrode using an ink jet spray method. U.S. patent application Ser. No. 13/616,804 to Kim et al. discloses a transparent panel and method of manufacturing a transparent panel where a conductive polymer layer is formed to make a transparent electrode. U.S. patent application Ser. No. 15/017,540 to Woodham discloses an apparatus and method for using a gel transfer combination having transparent conductive polymers and to separate proteins during an electrophoresis phase and thereafter transfer proteins to a transfer membrane after electrophoresis without transferring the gel from an electrophoresis apparatus to a separate protein blotting transfer apparatus. Opaque conductive polymers also have previously been described, but not in conjunction with electrophoresis and blotting. For example, U.S. Pat. No. 5,609,315 to Lepore describes electrically conductive opaque sheets made of polyimide and U.S. Pat. No. 4,702,371 to Hoshi describes electrically conductive portions of a plastic material to prevent electrostatic breakdown of electrical components such as those in integrated circuits.

One challenge in creating a single combination gel electrophoresis and protein transfer unit involves creating an apparatus where the user can visualize the degree of protein separation during electrophoresis and thereafter transfer the proteins to a blotting membrane without physically transferring the gel to the membrane. For such an apparatus to perform both electrophoresis and protein transfer, the plates must form the structural support for the gel, and also be able to transfer current through the gel supporting plates to a blotting membrane. The challenge is that the electrical current required to transfer proteins to the blotting membrane must run perpendicular to the current required to separate proteins during electrophoresis. Gel supporting plates that can be made rigid, transparent, and conductive would be ideal for use in such a gel and membrane combination unit.

One promising material that can provide rigidity, transparency, and conductivity are transparent metal compositions such as indium tin oxide (ITO). Compositions like ITO have been used in some applications where both conductivity and transparency are required, however, a considerable compromise must be made between conductivity and transparency. Likewise, transparent polymers such as conductive transparent plastics could be used, but there is also a compromise between conductivity and transparency. Furthermore, transparent conductive polymers are costly and may be cost prohibitive for commercial application such for the use in western blots.

Another problem with separating proteins within an electrophoresis gel is that if the user does not carefully monitor the protein separation phase, proteins may run off of the gel into the electrophoresis buffer. One way to prevent proteins from running off the gel is to have the electrophoresis power source on a timer so that after a pre-set amount of time has elapsed, the current shuts off. However, due to several variables (such as gel thickness and temperature), a timed shut-off may not allow the proteins to be optimally separated if the timer is set too short. If the timer is set too long, the proteins may run off the gel into the buffer. In addition, once the electrophoresis timer stops, proteins begin to diffuse within the gel. If the protein transfer step is not performed immediately after electrophoresis, protein bands may not be sufficiently defined.

Given the disadvantages of using a timer to end the electrophoresis phase, an alternative is to use an optical sensor that is capable of detecting the dye front of a sample loading buffer with known separation characteristics that is loaded into the wells of the gel as part of the protein running sample. When the optical sensor detects the dye front, the sensor communicates this information to the power source and shuts the current off, or controls the current in some other manner. Different types of electrophoresis power control devices have previously been described. One optical sensor linked power control device is described in PCT Appl. No. PCT/US2013/030220 to Asare-Okai et al. Asare-Okai discloses a controller with a sensor that is positioned adjacent to a gel matrix. The sensor includes a light source for emitting light into the gel matrix and a light detector disposed adjacent to the light sources for detecting light from the illuminated gel matrix. The controller is connected to a power source that provides a current across the electrophoresis phase electrodes. The controller is operable for turning off electrical power to the power source based on a change in the light emitted from the gel matrix due to migration of the tracking dye through the illuminated gel matrix.

U.S. Pat. No. 5,120,419 to Papp discloses a photoelectric electrophoresis controller. The controller is triggered by molecular dyes that are sensed by the photodetector when the dye reaches a predetermined position in the gel matrix, characterized by an observing photocell spaced from a reference photocell for comparison.

U.S. Pat. No. 5,268,568 to Lee discloses a marker dye band detector for gel electrophoresis using balanced light emitters. The device is capable of detecting a marker dye used in gel electrophoresis when the marker dye has reached a specific position in the gel. The device activates an alarm or shuts off the power source when the sensor detects the dye. Aare-Okai, Papp, and Lee do not disclose the use of optical sensors in a combination apparatus that can both separate and transfer proteins to a blotting membrane.

In view of the above limitations in the field, there currently exists a need in the industry for a device and associated method that can perform gel electrophoresis and protein transfer to a blotting membrane in one precast gel and transfer membrane combination unit.

All patents, patent applications, and non-patent references disclosed in the background and description of this application are hereby incorporated by reference for all purposes in their entireties.

SUMMARY OF THE INVENTION

The present invention advantageously fills the aforementioned deficiencies by providing gel electrophoresis and protein transfer using a single precast gel and blotting membrane combination unit using conductive polymers, the use of which provides a fast, reliable, and easy method to perform a hands-free protein separation followed by an efficient transfer of proteins to a blotting membrane.

The technology is defined as any technology, invention, know-how, method, composition, device, machine, product, consumable, formula and any combination thereof that relates to any use of conductive, semiconductive, and/or dissipative materials in the structure of a device for supporting an electrophoretic gel in which a blotting membrane is positioned adjacent to the gel, thereby permitting electrical current to flow through the gel in one direction during the protein separation phase and after the protein separation phase has completed, the current flows through conductive plate regions in a direction perpendicular to the direction of the flow of the current during the separation phase. This is accomplished without removing the gel from the precast gel and membrane combination unit.

The apparatus includes a first gel matrix supporting plate and a second gel matrix supporting plate substantially parallel to the first plate. The two plates have at least one region that is made from an opaque conductive polymer. The two plates sandwich a gel matrix and a blotting membrane, where the gel matrix is capable of separating proteins by size within the gel matrix when an electric current flows between electrodes on opposite sides of the y-axis of the gel matrix. The blotting membrane is capable of immobilizing proteins transferred from the gel matrix after protein separation without physically transferring the gel matrix to a blotting membrane after protein separation.

In one embodiment, the gel matrix supporting plate further includes a transparent static-dissipative polymer region. The transparent static-dissipative region is adjacent to the opaque conductive region along the y-axis of the opaque conductive polymer region. In this embodiment, the user can visualize a pre-stained molecular marker ladder having a loading dye that results in a dye front that migrates down the gel along the y-axis during electrophoresis.

One advantage of having both a transparent region (which is static-dissipative) and an opaque conductive region in a single unit is that these two features in combination allow the user to (1) see the molecular ladder separation through the transparent region while (2) not be constrained by the compromise usually encountered by having to choose between thickness, transparency, and conductivity in the region of the plate required for protein transfer during the transfer phase. By combining plates that have both a transparent region and an opaque conductive region, the user can determine the extent of protein separation by visualizing the extent of pre-stained molecular ladder separation (and migration of the dyes within the molecular ladder loading sample), while also having an apparatus where current can flow through opaque conductive regions to transfer the separated proteins to the blotting membrane. Since this molecular ladder does not need to be transferred to the blotting membrane for later protein analysis as the user can choose to run an alternate molecular marker ladder of choice in another well for transfer to the membrane, the transparent static-dissipative region of the plate does not have to be conductive. Therefore, only a narrow transparent region is required for the user to observe the pre-stained proteins and dye front, which serves as a proxy for the adjacent protein separation occurring behind the opaque conductive region.

In yet another embodiment, the apparatus also includes a thin layer of a less conductive gel (i.e. high percentage polyacrylamide) between the electrophoresis gel matrix and the blotting membrane. The electrophoresis gel matrix may include gels made from polyacrylamide, bis-Tris, Tris-acetate, etc. Immunoblotting membranes include those made from nitrocellulose, polyvinylidene difluoride (PVDF), etc.

Another embodiment is for a system to perform a single step electrophoresis and transfer of proteins. The system uses plastic insulators, a buffer tank and buffer tank lid. The tank includes an electrode assembly having a pair of electrophoresis separation phase electrodes, a pair of transfer phase electrodes, positive and negative electrode chambers, anode and cathode buffers, a cooling chamber, and a programmable power source to switch voltage from the separation phase electrodes to the transfer phase electrodes.

In yet another embodiment, the device includes a loading dye sensor to sense a dye front along the electrophoresis gel matrix. The sensor is connected in communication with circuitry in a detector that is electrically connected to the power source. When the sensor detects a dye front within the electrophoresis gel, the detector triggers the power source to switch from applying voltage from across the first and second separation phase electrodes to across the first and second transfer phase electrodes. This feature is advantageous because the user can program the power source first to separate proteins in the gel matrix, and then transfer the separated proteins to the blotting membrane. The sensor detects when the dye front has progressed a predetermined distance, which allows the user to avoid reliance on a timer, or avoid reliance on manually switching the voltage from the separation phase electrodes to the transfer phase electrodes.

In yet another embodiment, there is a method for protein separation and post-separation protein transfer onto a membrane. The method includes providing the gel and membrane combination unit described above within a liquid receptacle tank in a first orientation. After the user places the unit in the tank, the user applies a voltage across a pair of separation phase electrodes to separate biomolecules along a gel matrix, where the voltage across the pair of separation phase electrodes causes current to flow along the y-axis of the gel matrix in the first orientation as the conductivity of the gel is higher than that of the conductive polymers that encase it. The voltage causes the separating of biomolecules within the gel matrix by size. The voltage is then discontinued across the pair of separation electrodes. A voltage is then applied across a pair of transfer phase electrodes to transfer proteins from the gel matrix to a blotting membrane. This causes current to flow along a z-direction of the gel matrix in the first orientation. The current transfers biomolecules from the gel matrix to a blotting membrane. The steps of separating the biomolecules and transferring the biomolecules to the blotting membrane are performed without removing the unit from the tank, thereby combining the steps of electrophoresis and transfer in a single liquid receptacle tank without having to reorient the device between the separating step and transferring step.

The present invention owes its uniqueness to the fact that the apparatus and methods employ conductive polymers to house a precast gel membrane combination unit that acts as an insulator in one scenario, and an electrode in another scenario. This is advantageous for a device that separates proteins via electrophoresis in one direction using separation phase electrodes and transfers proteins perpendicularly out of the gel matrix to a blotting membrane via applying a voltage across a pair of transfer phase electrodes. The invention uses innovative conductive polymers with particular resistivity and along with transparent static-dissipative polymers in western blotting applications to solve fundamental problems found in current devices and methods. The present invention permits convenient, one-step protein separation and transfer of proteins for later analysis on a blotting membrane.

The present invention now will be described more fully hereinafter with reference to the accompanying drawings, which are intended to be read in conjunction with both this summary, the detailed description, and any preferred embodiments specifically discussed or otherwise disclosed. This invention may however be embodied in many different forms and should not be construed as limited to the embodiments set forth herein; rather, these embodiments are provided by way of illustration only to convey the full scope of the invention to those skilled in the art.

BRIEF DESCRIPTION OF THE DRAWINGS

These and other features and advantages of the present invention will become appreciated as the same becomes better understood with reference to the specification, claims, and drawings herein:

FIG. 2 shows a side view of a general setup of a precast gel and blotting membrane combination unit for electrophoresis and protein transfer showing directional electric current flow (arrows) to separate proteins within the gel matrix during electrophoresis;

FIG. 3 shows a side view of a general setup of a precast gel and blotting membrane combination unit for electrophoresis and protein transfer showing directional electric current flow during protein transfer to a blotting membrane perpendicular to the electric current flow that occurred during the electrophoresis phase;

DETAILED DESCRIPTION OF THE DRAWINGS

Figure 1:
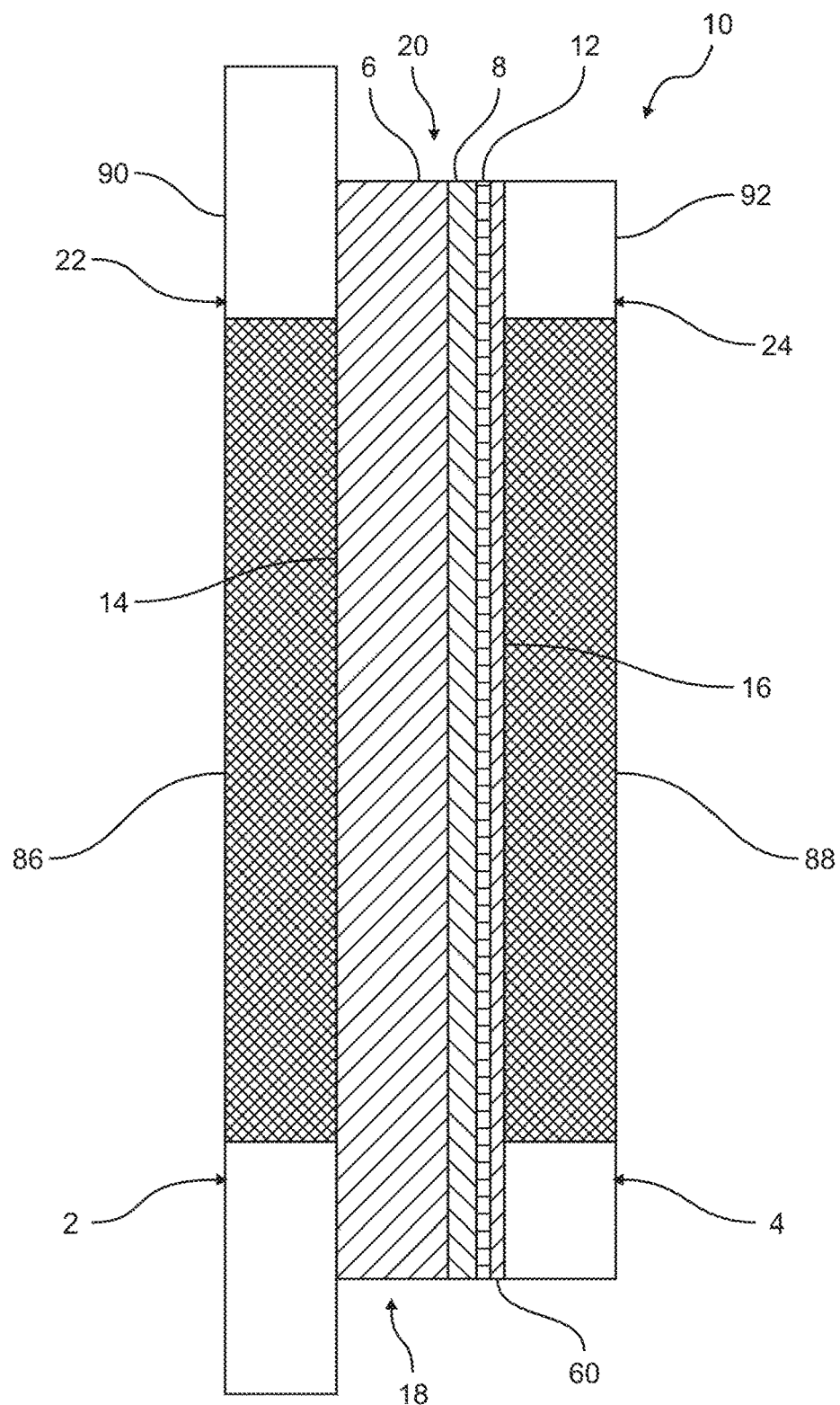
FIG. 1 shows a side view of the general setup of a precast gel and blotting membrane combination unit for electrophoresis and transfer, which includes a high conductivity gel and filter paper.

The invention now will be described more fully hereinafter with reference to the accompanying drawings, in which embodiments of the invention are shown. This invention may however be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

The terminology used herein is for the purpose of describing particular embodiments only, and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," "upper" or "top," "left" or "right," "above" or "below," may be used herein to describe one element's relationship to another element as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. The invention illustratively disclosed herein suitably may be practiced in the absence of any elements that are not specifically disclosed herein.

The present invention is directed to electrophoretic separation and transfer of proteins or other biomolecules with a precast gel and blotting membrane combination unit 10 using conductive polymers in at least one region of the unit. The polymers for use in the gel electrophoresis and transfer apparatus include conductive and transparent static-dissipative plastics. Electrophoresis may be performed using a variety of methods, including well-known western blot techniques employing the use of sodium dodecyl sulfate polyacrylamide gel electrophoresis (SDS-PAGE).

FIG. 1 shows a side view of one embodiment of the general setup of the precast gel matrix and blotting membrane combination unit 10 for separation of proteins during an electrophoresis phase and transfer of proteins during a transfer phase. The combination unit 10 has a first gel matrix supporting plate 2 and a second gel matrix supporting plate 4. Each plate 2, 4, has two distinct regions, (1) an opaque conductive region 86, 88, and (2) a transparent static-dissipative region 90, 92. The gel matrix 6 and blotting membrane 12 are sandwiched between the two plates 2, 4. Additionally, the gel 6 and membrane 12 may be separated by a thin layer of a low conductive (i.e. high percentage polyacrylamide) gel 8. During the electrophoresis protein separation phase, current flows from the upper surface 20 of the gel 6 to the lower surface 18 of the gel 6 (the current represented by the vertical arrows pointing downward in FIG. 2). This is accomplished by the particular conductivity/resistivity of the conductive polymers, in which their resistivity is higher than the gel 6. After the protein separation phase, the voltage is switched so that current flows through the conductive opaque regions 86, 88, thereby transferring the separated proteins to the blotting membrane 12 (the current represented by the horizontal arrows pointing right FIG. 3).

The Conductive Opaque and Transparent Static-Dissipative Regions

Generally, the polymers used to create support structures, such as the front and rear support plate of electrophoresis gels, are plastics, and therefore electrically insulating. However, there is a special class of polymers that intrinsically conduct or dissipate electricity at levels much higher than semiconductors (up to 1000 S/cm), and their conductivities/resistivities can be controlled through different methods of production. Conductive or dissipative polymers are organic polymers that conduct or dissipate electricity. Specifically, they offer electrical conductivity/dissipativity less than metals, and can have properties of plastics, such as transparency. The electrical properties (i.e. resistivity) can be fine-tuned using organic synthesis methods and dispersion techniques. Types of organic conductive polymers include polyacetylene, poly(pyrrole)s (PPY), polyanilines, poly(thiophene)s (PT), poly(3,4-ethylenedioxythiophene) (PEDOT), poly(p-phenylene sulfide) (PPS), poly(acetylene)s (PAC), poly(p-phenylene vinylene) (PPV), and others, such as those described in U.S. Pat. App. Pub. No. 20110050623 to Lee et al., and U.S. Pat. App. Pub. No. 20090032107. Generally, the electrical conductivity of a polymer is created by removing or adding an electron from the polymer's conjugated π-orbital via doping and the delocalization of electrons along the polymer backbone.

If a voltage is applied across typical insulating polymers, the polymer may discharge in a dangerous manner. To prevent discharge, the transparent polymer region of the plate where voltage is applied should be made from static-dissipative polymers, which generally have resistivity between $10^6$ to $10^9$ ohms per square. Static-dissipative polymers have little or no initial charges, prevent discharge to and from human contact, and are thus safer to use than non-static-dissipating polymers. In the present invention, by using a transparent static-dissipative polymer for the transparent regions, the user can visualize ladder migration in an electrophoresis gel and yet still remain safe when voltages are applied during the electrophoresis and transfer phases. Examples of static-dissipative polymers are disclosed in U.S. Pat. No. 4,729,925, U.S. Pat. No. 4,762,941, U.S. Pat. No. 5,968,656, U.S. Pat. No. 5,828,931, U.S. Pat. No. 5,798,060 U.S. Pat. No. 7,214,757, and U.S. Pat. No. 8,653,177, the disclosures of which are incorporated by reference herein. Compositions of static-dissipative polymers comprise or consist of at least one of polyamide-imides, polytetrafluoroethylene (PTFE), polyetheretherketones, polyetherimides, polyetherimides and their derivatives.

Gel Matrix

The electrophoresis gel matrix 6 is a slab gel and can be made from a variety of electrophoresis-supporting materials, including acrylamide, bisacrylamide, polyacrylamide, Tris-glycine, bis-Tris, Tris-acetate, cellulose acetate, agarose, silica, and other materials, as well as such materials in treated or derivatized form known among those skilled in the art. Agarose gels would typically be used for DNA and RNA analysis, and polyacrylamide, Tris-glycine, bis-Tris, and Tris-acetate gels for protein analysis. Typical resolving gels for protein analysis are made from between 6% and 15% polyacrylamide. The same techniques that have been described for use of the invention for protein separation and blotting can also be used for separation and blotting of DNA and RNA with the use of the appropriate gel.

In preferred embodiments, a bis-Tris polyacrylamide gel is comprised of 10% to 12% bis-Tris polyacrylamide and a Tris-acetate polyacrylamide gel is comprised of approximately 7%-10% Tris-acetate polyacrylamide, but values may lie outside these ranges depending on the size of the protein that the user wishes to analyze or probe in the sample. The dimensions of the electrophoresis gel 6 are typically rectangular and in a preferred embodiment are approximately 10 cm×10 cm, but may vary depending on the number of samples to be run simultaneously, the type of sample, and the sample volume.

In a preferred embodiment, the electrophoresis gel and transfer membrane combination unit 10 is less than 0.5 cm thick, but could also be designed thicker. Additionally, a stacking gel (not depicted) on top of the electrophoresis gel 6 may also be included above the primary electrophoresis gel 6, and made from a lower percentage of the equivalent corresponding material used in the electrophoresis gel 6. Stacking gels are well known in the art as a tool to concentrate and pack all the proteins of the sample into one band before separation occurs. Differences in the pH and acrylamide concentration at the interface of the stacking and separating gel 6 functions to compress the sample at the interface and provides better resolution and sharper bands in the separating gel 6. A standard electrophoresis plastic comb is placed in the primary electrophoresis gel or stacking gel to create wells 84 in the gel where the user loads the protein-containing samples.

Blotting Membrane

Adjacent to the gel 6 is a blotting membrane 12, also known as a transfer membrane, immobilization membrane, or blotting paper. The blotting membrane 12, may be made from a variety of blotting materials, such as nitrocellulose, PVDF, nylon, or other materials known in the art used for immobilizing proteins on a sheet.

As depicted in FIG. 1, the gel 6 and membrane 12 may be separated by a thin low conductivity gel 8. The low conductivity gel 8 is positioned between the blotting membrane 12 and electrophoresis gel 6. The low conductivity gel 8 prevents the direct contact of the blotting membrane 12 with the electrophoresis gel 6 during the electrophoresis phase. Since proteins have a high affinity to blotting membranes 12, the low conductivity gel 8 prevents proteins from binding to the surface of the membrane 12 during electrophoresis.

Gel Supporting Plates

Each plate 2, 4 is made from a combination of opaque conductive materials and static-dissipative materials. Opaque conductive materials comprise or consist of at least one of conductive polyethylenes such as Tivar® 1000 EC and Lennite® CN, conductive acrylonitrile-butadiene-styrenes (ABS) such as Absylux® CN, conductive acetal (polyoxymethylene or POM) copolymers such as Pomalux® CN-F or Pomalux® CN-SS, conductive polypropylenes such as Propylux® CN-P or Propylux® CN-F, conductive polyetherimides such as Tempalux® CN, conductive polyaryletherketones such as TecaPEEK™ ELS, conductive polycarbonates such as Zelux® CN-P or Zelux® CN-SS, (all currently available through Boedeker Plastics, Inc.) or, other known conductive polymers, all of which can can be manufactured with volume resistivities in the range of $10^3$ to $10^5$ ohm-cm. The generic equivalents of the above mentioned conductive polymers are also suitable for use in the conductive plates 2, 4. In addition, the plates 2, 4, may be doped with conductive powder, such as carbon or stainless steel powder, or may be made from intrinsically conductive polymers.

Transparent static-dissipative compositions include compositions made from polyanilines, polypryrrols, polythiophenes, polycarbonates such as PC-300™ available through SciCron Technologies, or other known transparent static-dissipative polymers. Each plate 2, 4 has an opaque region 86, 88 made from the opaque conductive polymers. In a preferred embodiment, the polymer used for the opaque conductive region 86, 88 has a volume resistivity in the range of approximately $10^3$-$10^5$ ohm-cm, whereas the transparent dissipative region 90, 92 has a volume resistivity in the range of approximately $10^5$-$10^9$ ohm-cm. Since the conductivity of the opaque conductive regions 86, 88 that form the support plates of the gel 6 is less than that of typical conductors (such as metals) the opaque conductive region 86, 88 may be considered a semi-conductor (at least compared with the conductivity of typical metals that have a volume resistivity typically around $10^{-6}$ ohm-cm and the volume resistivity of insulators, typically around $10^{18}$ ohm-cm). This semi-conductive quality of the opaque conductive region 86, 88, where the opaque conductive region 86, 88 is not as conductive as the gel 6, cause the plates 2, 4 to act as insulators during the electrophoresis step and do not interfere with the protein separation electrophoresis phase. During the protein separation electrophoresis phase, the electrical current takes the path of least resistance through the gel 6 and not through the plates 2, 4 because the plates 2, 4 have higher resistivity than the gel 6. This feature of the opaque conductive region being less conductive than the electrophoresis gel overcomes problems addressed in the prior art, such as in U.S. Pat. No. 4,994,166 to Fernwood, where plate electrodes made from highly conductive materials (such as those made from metals) may nullify an electric field around a gel, and therefore could prevent separation of proteins during electrophoresis.

Surrounding the opaque conductive region 86, 88 is the transparent static-dissipative region 90, 92. The opaque conductive region 86, 88 of each plate 2, 4 is positioned adjacent to the transparent region 90, 92. The opaque conducive region 86, 88 depicted in FIG. 4, shows the transparent static-dissipative region framing the opaque conductive region 86, 88 on three sides: (1) above the opaque region 86, 88 along the x-axis of the gel, (2) on one side of the opaque conductive region 86 along the y-axis of the gel, and (3) below the opaque region 86, 88 the along the x-axis of the gel. The plates 2, 4 may have pedestals 80 (See FIG. 9) on their side edges to allow for the creation of a cavity that forms the boundaries of the electrophoresis gel 6 and blotting membrane 12.

The transparent static-dissipative regions 90, 92 allows the user to observe the loaded samples in the gel 6 and also observe the migration of a molecular marker ladder 94 in a lane adjacent to the opaque conductive region 86, 88 so that the user can deduce the extent of protein separation during electrophoresis. Moreover, as typical plastics are insulative, they cannot be used adjacent to the conductive materials as charge could build up during the protein transfer step, thereby creating a discharge hazard. The combination of both transparent static-dissipative polymers with opaque conductive polymers reduces this hazard. In addition, the entirety or near entirety of the plates 2, 4 could be made from transparent conductive or semi-conductive polymers or a combination of the two, or a combination of transparent and opaque transparent conductive and semi-conductive polymers.

Figure 4A:
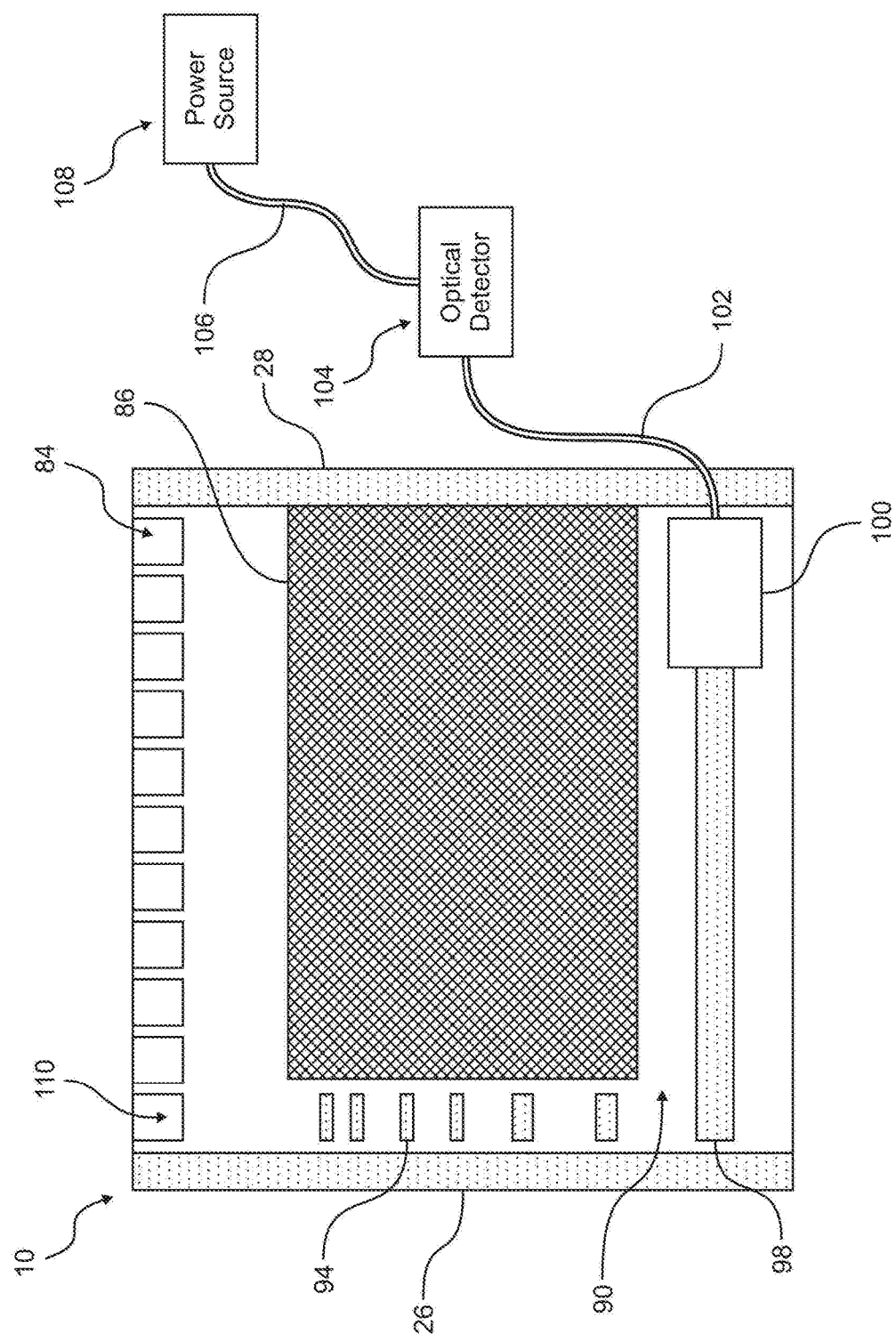
FIG. 4A shows a front view of the general setup of the precast gel and blotting membrane combination unit for electrophoresis and protein separation having transparent and non-transparent regions of a gel matrix support plate.

In some embodiments, such as the one illustrated in FIG. 4A, only a single loading lane 110 is visible in the transparent static-dissipative region 90, 92. A single loading lane 110 is all that should be necessary to visually determine the extent of protein separation that has occurred during electrophoresis because protein separation is correlated with pre-stained molecular marker ladder separation.

Figure 8:
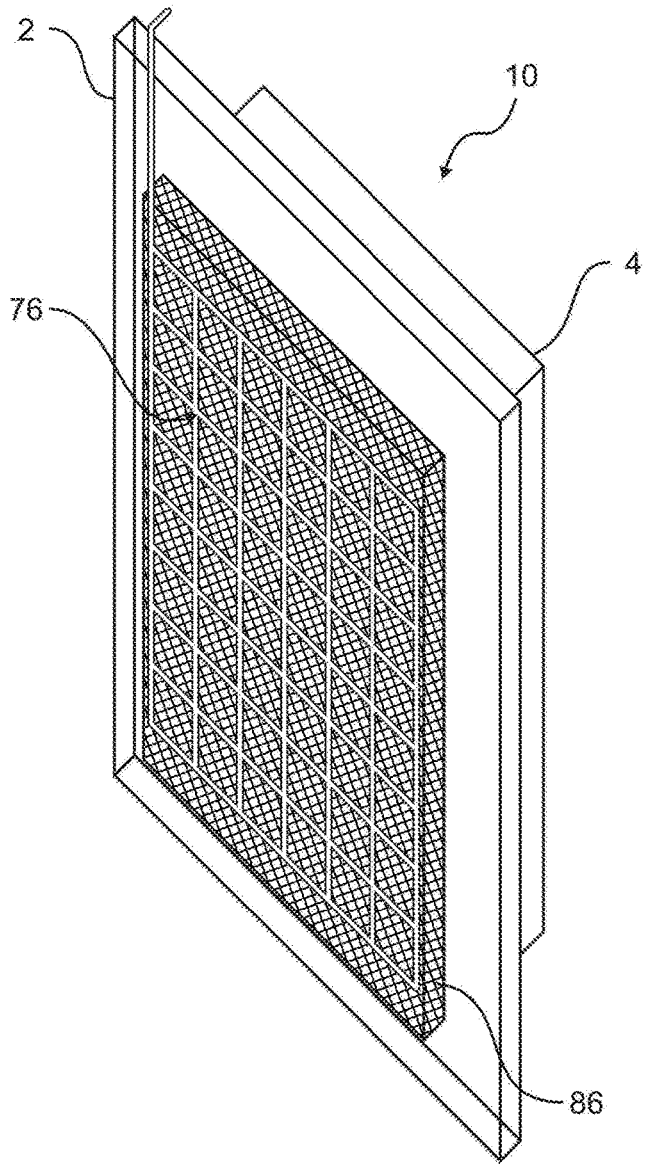
FIG. 8 shows a perspective view of an embodiment of the precast gel and blotting membrane combination unit having a conductive wire mesh.

To ensure a substantially equal electric field emanating from all areas of the opaque conductive regions 86, 88 during the transfer phase, the opaque conductive region 86, 88 may have one or more thin wires (or nanowires) 76, 82 disposed on the plates' outer surfaces, as depicted in FIG. 8.

In one embodiment of the combination unit 10, adjacent to the blotting membrane 12 is a filter paper 60. The filter paper 60 is sandwiched between the blotting membrane 12 and the second gel matrix supporting plate 4. Filter paper 60, when wet, acts as an ion reservoir, thereby aiding in the transfer of biomolecules to the blotting membrane 12 during the transfer phase. Filter paper 60 also ensures that the blotting membrane 12 stays wet. The blotting membrane 12 and filter paper 60 may be pre-wet prior to assembly of the combination unit 10, often using a solution containing methanol or other wetting buffer. The filter paper 60 may also be wet from the buffer solution used during the electrophoresis and transfer phases.

Figure 4B:
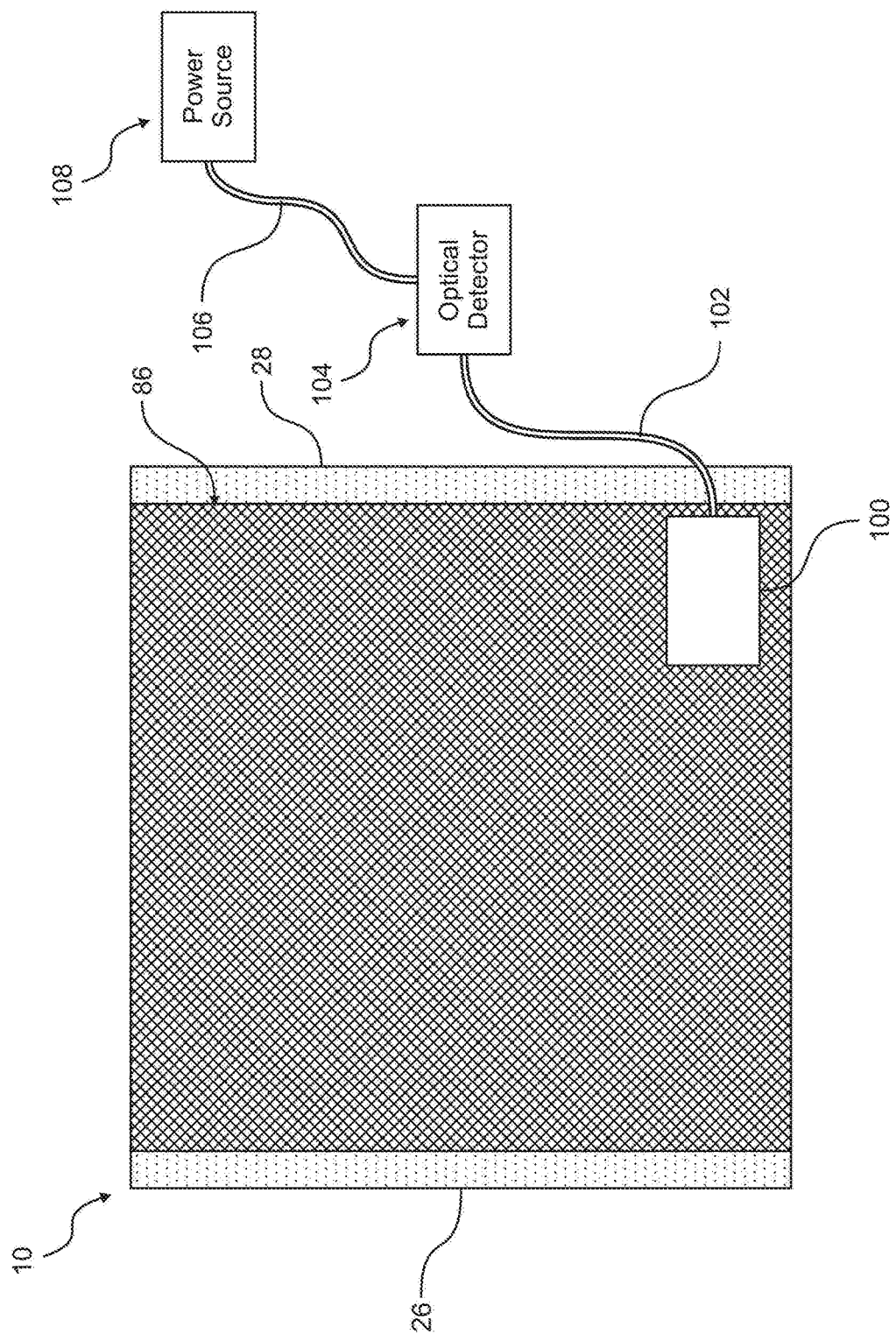
FIG. 4B shows a front view of the general setup of the precast gel and blotting membrane combination unit for electrophoresis and protein separation having only a non-transparent plate.

Returning again, FIG. 4A, FIG. 4B depicts the front view of the precast gel and blotting membrane combination unit 10 for electrophoresis and transfer. During the electrophoresis protein separation phase, as voltage is applied across the top and bottom of the gel 6, proteins migrate vertically from the top of the gel 6 to the bottom of the gel 6 along its y-axis. In one embodiment, there are two non-conductive insulative plastic strips 26, 28 that flank the sides of the gel 6, or could be made from projections or pedestals of the plates themselves. The strips 26, 28 are also sandwiched between the plates 2, 4, or are extensions of the plates to establish the space for and direct current through the gel 6 during the electrophoresis phase. These strips, projections, or pedestals also provide structural support and rigidity to the unit 10. The transfer of proteins during the transfer step is along the z-axis, (i.e. perpendicular to the y-axis direction of protein separation and also perpendicular to the x-axis loading well direction of the gel).

Figure 5:
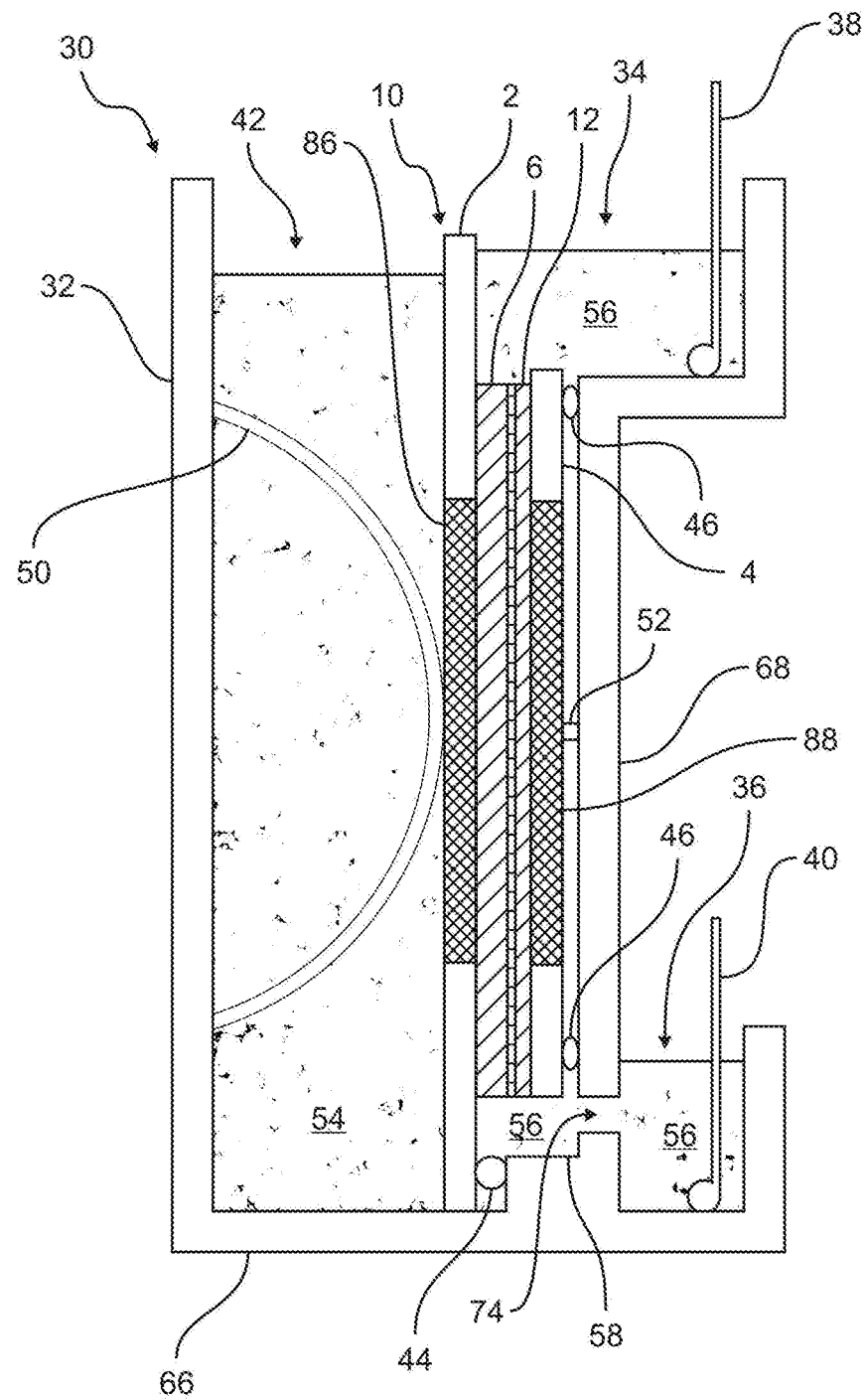
FIG. 5 shows a cross sectional side view of the precast gel and blotting membrane combination unit within an electrophoresis and transfer tank.

The gel and blotting membrane unit 10 is placed in a tank apparatus 30 in order to allow current to flow along the y-axis and z-axis of the gel and blotting membrane unit 10. One such apparatus to perform both electrophoresis and blotting is illustrated in FIG. 5. FIG. 5 depicts the tank apparatus 30 together with the precast gel and blotting membrane combination unit 10, which together is a system for performing both the electrophoresis separation phase and transfer phase. The tank apparatus 30 is a liquid receptacle that includes a front panel 32, rear panel 68, first side panel 70, second side panel 72, bottom panel 66, lip 58 on the rear panel 68, and a lid (not shown). The lip 58 may be a variety of shapes but in a preferred embodiment is substantially U-shaped along the inner walls of the first and second side panels 70, 72 of the tank apparatus 30.

Typical for a protein separation gel, the combination unit may be submerged in an electrolyte containing buffered solution such as Tris-acetate-ethylenediaminetetraacetic acid (EDTA) (TAE), 2-(N-morpholino)ethanesulfonic acid (MES), or 3-(N-morpholino)propanesulfonic acid (MOPS). Other buffers may be used depending on the type of gel used in the precast gel and blotting membrane combination unit 10. For example, a TAE buffer may be used for Tris-acetate polyacrylamide gels, whereas MES or MOPS buffers may be used for bis-Tris polyacrylamide gels. The buffers in this system should be efficient for both the electrophoresis phase and transfer phase.

The tank apparatus 30 has an upper chamber 34 and a lower chamber 36. A first separation phase negative electrode (cathode) 38 is disposed within the upper chamber 34. A second separation phase positive electrode (anode) 40 is disposed within the lower chamber 36. The first and second separation phase electrodes 38, 40 are each connected to a programmable power source 108 to power the separation electrodes 38, 40. The desired voltage for electrophoresis between the first and second separation phase electrodes 38, 40 is generally between 80 and 150 volts, but may be lower or higher depending on the desired rate of separation. The power source 108 employs switching means for electrical isolation of the separation phase electrodes 38, 40 from the transfer phase electrodes 50, 52. The switching means include manual switching means through the use of a button, toggle or any other electro-mechanical means to change current from one set of electrodes to a different set of electrodes. The power source may also include automatic means to switch the applied voltage from one set of electrodes to a different set of electrodes, such as by automatic switching after a pre-set amount of time, or switching after an optical detector senses the presence of a dye front in the gel. The power source is connected to optical detector and to the anodes 38, 50 and cathodes 40, 52, of the apparatus.

As depicted in FIGS. 4A and 4B, and with respect to the inclusion of an optical sensor as a means for automatic voltage switching, the gel and blotting membrane combination unit 10 may include an optical sensor 100, which can be connected to a separate optical detector 104 having circuitry to detect dye within the gel 6. The optical detector 104 may be physically connected to the sensor 100 by wire 102 or connected wirelessly. The optical detector 104 is connected to a power source 108. The optical detector may also be connected to the power source 108 by wire 106 or wirelessly, and communicate power control information to the power source 108, such as through WiFi, radio signal, a physical connection, or any other of a number of known means in the art to communicate information to control output.

The use of optical sensors and detectors in electrophoresis systems is known in the art and may be incorporated into the present invention. PCT Application No. PCT/US2013/030220, U.S. Pat. No. 5,120,419, and U.S. Pat. No. 5,268,568 all disclose different devices and methods to use an optical sensor in an electrophoresis device, the disclosures of which are incorporated by reference herein. In the present embodiment, as the sensor 100 and detector 104 detect the presence of a dye front 98, the detector transmits a signal to the power source 108 to switch voltage from the electrophoresis electrodes 38, 40 to the transfer electrodes 50, 52.

In another embodiment, such as the one depicted in FIG. 4B, the gel and blotting membrane combination unit 10 does not include a transparent region in the plate 2, 4, but instead only includes the opaque conductive region 86, 88. In this type of embodiment, the user would not visualize the molecular ladder 94 and therefore not visually confirm separation of proteins. However, one or more sensors 100 are placed within the conductive opaque regions 86, 88 to detect the presence of a dye. The optical detector 104 triggers the power source 108 to switch voltage from the separation phase electrodes 38, 40 to the transfer phase electrodes 50, 52, when the detector 104 detects the dye. As dye passes in front of a sensor 100 positioned at a strategic location along the gel 6, the presence of dye indicates sufficient protein separation and the next step of protein transfer to a membrane can begin.

To accomplish electrophoresis and transfer of proteins within the tank apparatus 30, the upper chamber 34 and lower chamber 36 are each filled with a buffer solution 56. The chambers 34, 36 are electrically connected to each other via the electrically conducting gel and transfer combination unit 10. The buffer solution 56 and gel 6 allow negative charges to pass from the first separation electrode 38, through the buffer 56 in the upper chamber 34, then through gel 6 to buffer 56 in the lower chamber 36, and finally to the second separation phase electrode 40. This flow of current, which generally forces to migrate down through the gel, is accomplished in part due to the relatively low conductivity of the conductive and static-dissipative polymers housing the gel, which have a higher resistance than the gel 6.

In one embodiment, the buffers 56 will have a volume resistivity of approximately 10-200 ohm-cm and gels may have similar volume resistivities, typically between 100-300 ohm-cm. The opaque conductive regions 86, 88 will have volume resistivities in the range of $10^3$ to $10^5$ ohm-cm, and the static-dissipative regions 90, 92 will have volume resistivity of $10^5$ to $10^9$ ohm-cm. These ranges will allow for the electric current to flow through the gel during the separation phase when a power source is applied to separation electrodes 38, 40 rather than through the first and second plates 2, 4. Then, when voltage is applied across the transfer phase electrodes 50 and 52, the electric current flows substantially perpendicular to the length of the y-axis of gel 6 through the membrane 12, to the second plate 4, thereby allowing the proteins to adhere to the blotting membrane 12 during the transfer phase.

While these ranges have been described in terms of exemplary embodiments, it is to be understood that they are not limiting, whereas any embodiment in which the buffer 56 and gel 6 have a reasonably lower resistivity than the conductive polymers (i.e. plates 2, 4) that house them, and conversely that the conductive polymers (i.e. plates 2, 4) have a reasonably higher conductivity than the buffer 56 and gel 6, will allow for the described separation and transfer phases.

The rear panel 68 has one or more openings 74 in its lower region to allow the buffer solution 56 from the lower chamber 36 to fill up to the lower surface 18 of the gel 6 to provide an electrical connection from the second separation electrode 40 to the gel 6. The buffer solution 56 in the upper chamber 34 and lower chamber 36 may be the same buffer solution, or may be different buffer solutions, where in some embodiments, the buffer solution 56 in the upper chamber 34 may include an antioxidant.

The wires electrify the buffer solution 56, thereby causing the solution in the upper chamber 34 to act as the cathode (−) and solution in the lower chamber 36 to act as the anode (+). Proteins in a sample buffer containing sodium dodecyl sulfate (SDS), or other buffers that are well known in the art, impart proteins with negative net charge so that when the proteins are in the gel 6, the proteins move from the cathode (−) 38 to the anode (+) 40 due to the electromotive force (EMF) created by the power source. By placing proteins in wells 84 and applying an electric field along the y-axis of the gel, the proteins move through the gel 6 at different rates, determined largely by their masses.

As illustrated in FIG. 5, the buffer solution 56 in the upper chamber 34 and lower chamber 36 are not in buffer contact with each other, but are still in electrical contact. The buffer solutions 56 in the top and bottom chambers 34, 36 are physically separated by the gel and blotting membrane combination unit 10. Gaskets 44, 46 prevent the buffer solution 56 from filling the entirety of the tank apparatus 30. A rear panel gasket 46 is disposed on the inner surface of the rear panel 68 of the tank apparatus 10. The rear panel gasket 46 prevents buffer solution 56 from contacting a transfer electrode 52, which would cause unwanted electrical current flow during the separation phase if buffer filled the entire tank and all sides of the combination unit 10. Additionally, the apparatus 30 may include a lip gasket 44 disposed along the outer surface of the lip 58. The lip gasket 44 prevents buffer solution 56, necessary for the separation phase, from contacting the cooling solution 54 used in the cooling chamber 42. The cooling chamber can be filled with water, buffer, or other types of coolant. Gaskets in the preferred embodiments may be made from rubber, silicone, and other flexible materials commonly used to form seals that prevent liquid seepage.

Figure 6:
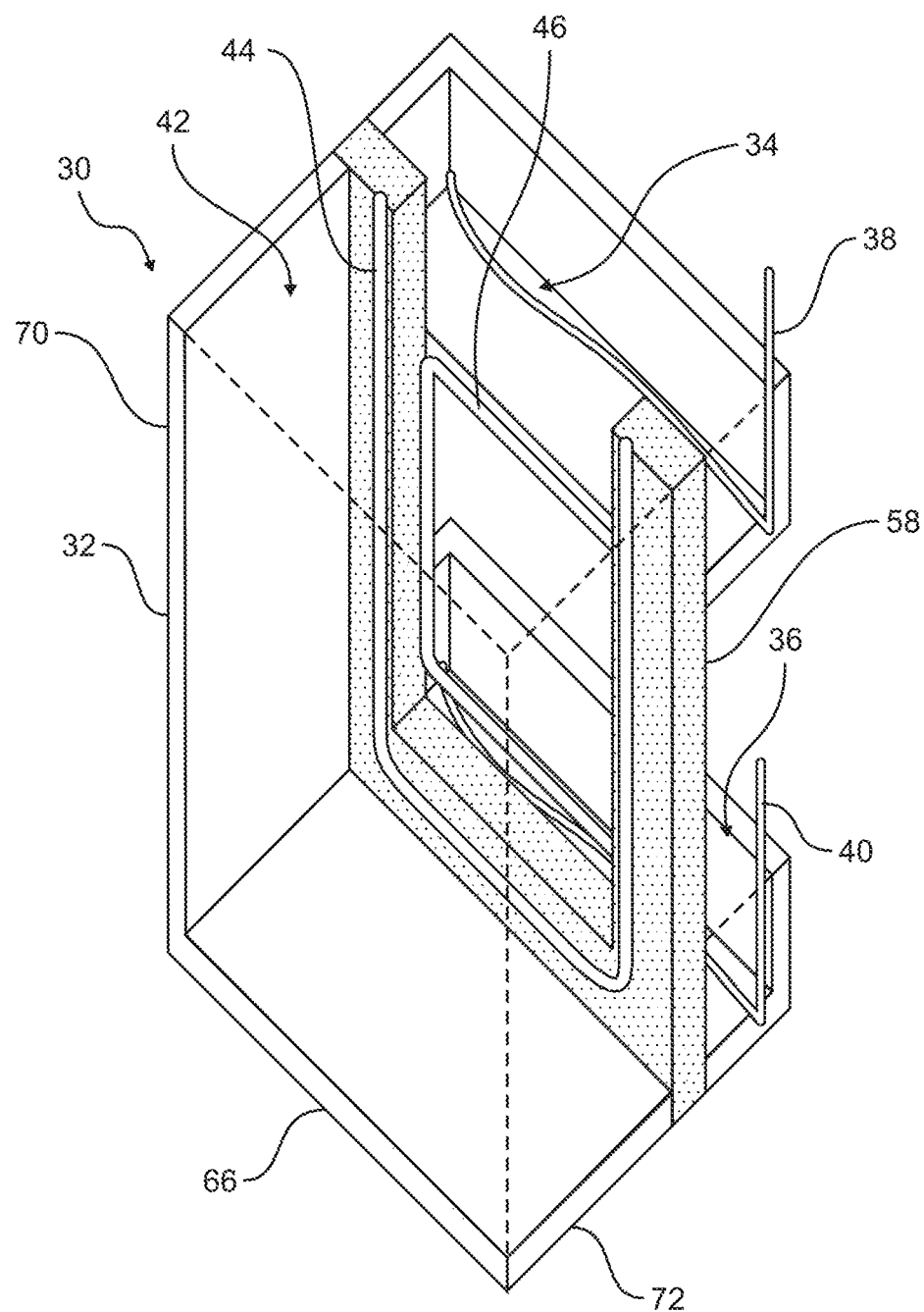
FIG. 6 shows a perspective view of the electrophoresis and transfer tank without the precast gel and blotting membrane combination unit placed inside the tank.

The rear panel gasket 46 is positioned so that when the precast gel and membrane combination unit 10 is placed within the tank apparatus 30, the outer surface of the second plate 4 is pressed against the gasket 46. The lip gasket 44 is positioned so that the inner surface of the first plate 2 is pressed against the lip gasket 44. As shown in FIG. 6, the rear panel gasket 46 is a continuous loop along the inner surface of the rear panel 68. The lip gasket 44 has an open shape with a bottom region connected to two side regions. The lack of a rubber sealing structure on the top allows the buffer 56 to be in electrical contact with the top of gel 6. In sum, the gaskets 44, 46 are positioned such that when the precast gel and membrane combination unit 10 is placed correctly within the tank apparatus 30, the gaskets 44, 46 form seals that keep the upper chamber 34 and lower chambers 36 (necessary for the electrophoresis phase) separate from the cooling chamber 42 and other structures required during the protein transfer phase.

Another feature of the embodiment that prevents the upper and lower chambers 34, 36, from being in electrical contact with the cooling chamber 42 is that the first plate plate 2 is larger than the second plate 4 as depicted in FIGS. 1, 5, and 7-9. In a preferred embodiment, the first plate is approximately 12 cm×12 cm and the second plate 4 is approximately 10 cm×10 cm (approximately the same dimensions of the gel 6). The larger first plate 2 allows for the first plate 2 to contact the lip gasket 44, and allows the smaller second plate 4 to be in contact with the rear panel gasket 46. The smaller second plate 4 allows the buffer solution 56 to pass over and under the second conductive plate 4 in the upper chamber 34 and lower chamber 36, respectively, but not pass through the larger first plate 2. This setup prevents the buffer solution 56 from entering into the cooling chamber 42 and contacting the transfer electrodes 50, 52 used during the protein transfer phase.

After the protein separation phase, when the proteins have been separated by size vertically along the y-axis of gel 6, voltage is switched from the separation electrodes 38, 40 to transfer electrodes 50, 52, which forces the proteins to transfer from the gel 6 to the blotting membrane 12. The opaque conductive region 86 is in electrical contact with a first transfer electrode 50 connected to the power source 108, and the second conductive opaque region 88 is in electrical contact with a second transfer electrode 52.

In the embodiment shown in FIG. 5, the first transfer electrode 50 is an arc shaped metal brace to provide sufficient tension to hold the precast gel and membrane combination unit 10 in place against the gaskets 44, 46 to form the different chambers 34, 36, 42 of the apparatus 30. The transfer electrode 50 could also be a separate element from the structure that braces the precast gel and membrane combination unit 10 inside the tank 30 against the various gaskets 44, 46. In other embodiments, the first transfer electrode 50 may be separated into two or more brackets (e.g. one on the left side, one on the right side) so that the user can still view the gel 6, but the precast gel and combination unit 10 is still held firmly in place within the tank 30. Other types of braces can also be placed inside the cooling chamber 42 without departing from the spirit of the invention as long as there is tension and electrical contact between the transfer electrode 50 and the first plate 2.

The second transfer electrode 52 is disposed along the inner surface of the rear panel 68 and acts as the anode (+) during the protein transfer phase. In the embodiment shown in FIG. 5, the second transfer electrode 52 has a spring or recoil action so that the transfer electrode 52 makes sufficient contact with the second plate 4. In other embodiments, the transfer electrode 52 may be a separate element from an element having the spring or recoil action to help brace the precast gel and membrane combination unit 10 inside the tank 30 against an opposing bracing member.

An electrical power source 108 connects the first transfer electrode 50 with the second transfer electrode 52 and voltage is applied across the transfer electrodes 50, 52 such that the first plate 2 acts as the cathode (−) and second plate 4 acts as the anode (+) during the protein transfer phase. The power source 108 shall provide enough current to achieve sufficient transfer of the proteins from the gel 6 to the transfer membrane 12 housed within the precast gel and membrane combination unit 10. Typical voltages applied across the transfer electrodes 50, 52 to achieve sufficient current flow to transfer proteins to the blotting membrane 12 are between 5 to 30 volts, but higher voltages can also be applied without damaging the gel 6 or blotting membrane 12.

FIG. 6 is a perspective view of the tank apparatus 30 without the precast gel and blotting membrane combination unit 10. The combination unit 10 would be placed adjacent to (on the left side) of the lip 58 having the lip gasket 44. Since the first plate 2 is larger than the second plate 4, the first plate 2 lays on the outer surface, while the electrophoresis gel 6, low conductivity gel 8, transfer membrane 12 and filter paper 60 are positioned within the inner cavity of the lip 58 and the second plate 4 is pressed against the rear panel gasket 46.

Figure 7:
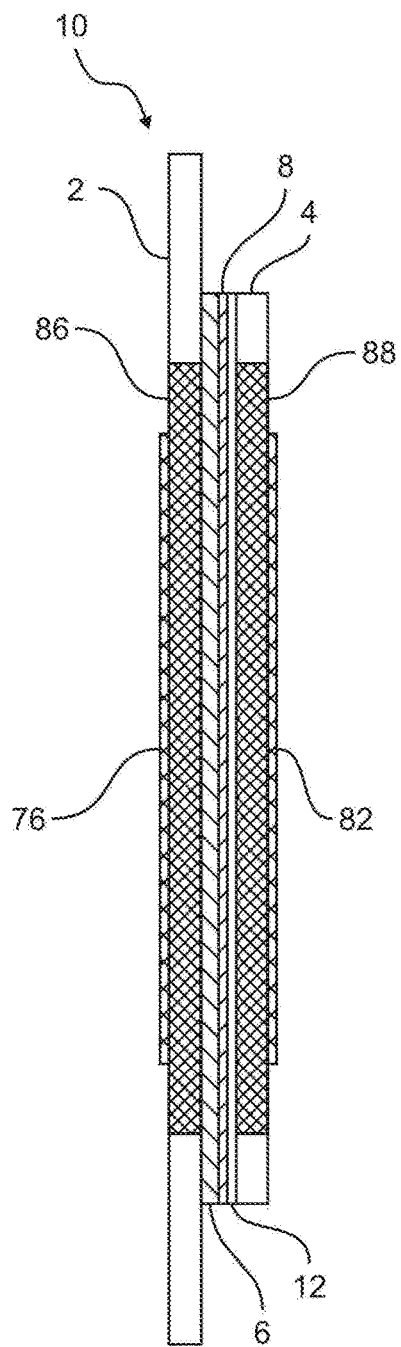
FIG. 7 shows a side view of an embodiment of the precast gel and blotting membrane combination unit having a conductive wire mesh.

FIGS. 7 and 8 show another embodiment of a precast gel and membrane combination unit 10. Within or on the opaque conductive region 86 are a plurality of conductive wires or conductive mesh 76, which may be arranged in a grid or array. The mesh 76 distributes electric current along the opaque conductive region 86. In addition to a wire mesh disposed on or within the first opaque conductive region 86 is a second wire mesh 82 that may be disposed on or within the second opaque conductive region 88 to evenly distribute charge along the second opaque conductive region 88. The wire meshes 76, 82 ensure that electric charge is evenly distributed along the conductive regions 86, 88.

Figure 9:
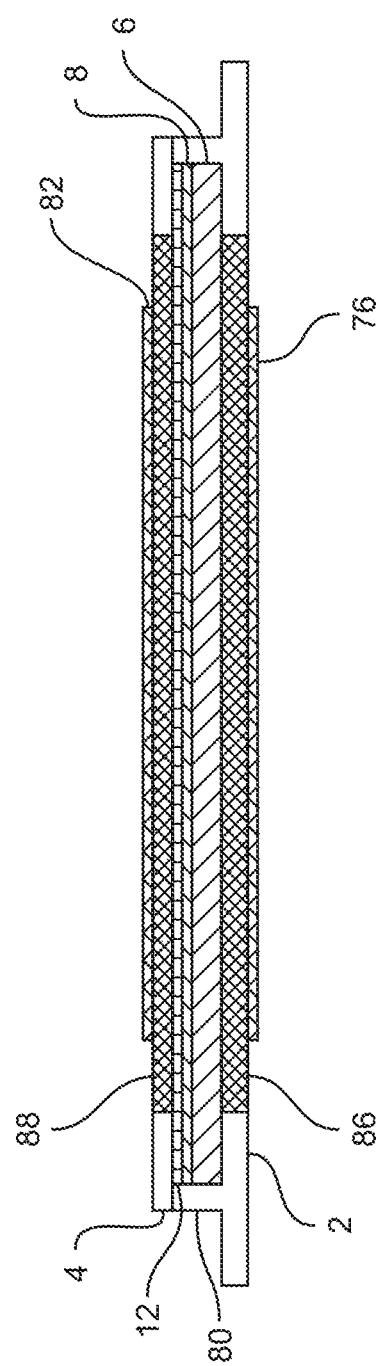
FIG. 9 shows a top view of an embodiment of the precast gel and blotting membrane combination unit having projections on one plate to create a gap for the gel and blotting membrane.

FIG. 9 illustrates another example of the precast gel and membrane combination unit 10. This embodiment includes two pedestal projections 80 in the static-dissipative region of the first plate 2 abutting the inner surface of the second plate 4. The second plate 4 rests over the pedestals 80, thereby forming a cavity or gap between the inner surface of the first plate 2 and the inner surface of the second plate 4. The gap size may vary depending on the desired thickness of the gel 6. In a preferred embodiment, the gap between the first and second plates 2, 4 ranges from about 0.1 cm to about 0.5 cm. The gap holds the various previously described components needed for proper separation and blotting of proteins in the precast gel and membrane combination unit 10, such as the electrophoresis gel 6, low conductivity gel 8, transfer membrane 12, and filter paper 60.

While the invention has been described in terms of exemplary embodiments, it is to be understood that the words which have been used herein are words of description and not of limitation. As is understood by persons of ordinary skill in the art, a variety of modifications can be made without departing from the scope of the invention defined by the following claims, which should be given their fullest, fair scope.

I claim:

1. A method for separation and post-separation transfer of biomolecules to a blotting membrane, the method comprising the steps of:

providing a device within a liquid receptacle tank in a first orientation, wherein the device comprises: a first gel matrix supporting plate having at least one region made from an opaque semi-conductive polymer; a second gel matrix supporting plate substantially parallel to the first gel matrix supporting plate, the second gel matrix supporting plate having at least one region made from an opaque semi-conductive polymer; a gel matrix between the first and second gel matrix supporting plates, wherein the gel matrix is capable of separating biomolecules such as proteins by size within the gel matrix when an electric current flows between electrodes of opposite polarity on opposing sides of the gel matrix; and, a blotting membrane between the gel matrix and at least one of the first and second gel matrix supporting plate, wherein the blotting membrane is capable of immobilizing biomolecules such as proteins transferred from the gel matrix after separation without physically transferring the gel matrix to the blotting membrane;

applying a voltage across a pair of separation phase electrodes to separate biomolecules along a gel matrix, wherein the voltage across the pair of separation phase electrodes causes current to flow along a y-axis of the gel matrix in the first orientation and separate biomolecules within the gel matrix according to size;

separating biomolecules within the gel matrix by size;

discontinuing applying the voltage across the pair of separation electrodes;

applying a voltage across a pair of transfer phase electrodes to transfer biomolecules from the gel matrix to a blotting membrane, wherein applying the voltage across the pair of transfer phase electrodes causes current to flow along a z-direction of the gel matrix in the first orientation;

transferring biomolecules from the gel matrix to a blotting membrane;

wherein the steps of separating the biomolecules and transferring the biomolecules to the blotting membrane is performed without removing the device from the liquid receptacle tank, thereby combining the steps of electrophoresis and transfer in a single liquid receptacle tank without having to reorient the device between the separating step and transferring step.

2. The method of claim 1 wherein the steps of discontinuing applying the voltage across the pair of separation electrodes and applying a voltage across a pair of transfer phase electrodes is triggered by detecting the presence of dye within the gel matrix.

* * * * *